US00PP24130P2

(12) United States Plant Patent
Miyazaki

(10) Patent No.: US PP24,130 P2
(45) Date of Patent: Dec. 31, 2013

(54) ***PHLOX* PLANT NAMED 'SUNPHLOSIRO'**

(50) Latin Name: *Phlox drummondii*
Varietal Denomination: Sunphlosiro

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 92 days.

(21) Appl. No.: 13/385,162

(22) Filed: Feb. 6, 2012

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Howard Locker
(74) *Attorney, Agent, or Firm* — C. A. Whealy

(57) ABSTRACT

A new and distinct cultivar of *Phlox* plant named 'Sunphlosiro', characterized by its compact and mounding plant habit; vigorous growth habit; freely branching and flowering habit; long flowering period; white-colored flowers; and good garden performance.

1 Drawing Sheet

Botanical designation: *Phlox drummondii.*
Cultivar denomination: 'SUNPHLOSIRO'.

BACKGROUND OF THE INVENTION

The present invention relates to a new and distinct cultivar of *Phlox* plant, botanically known as *Phlox drummondii* and hereinafter referred to by the name 'Sunphlosiro'.

The new *Phlox* plant is a product of a planned breeding program conducted by the Inventor in Higashiomi, Shiga, Japan. The objective of the breeding program was to create new compact, mounding and freely branching *Phlox* plants with attractive flower coloration.

The new *Phlox* plant originated from a cross-pollination made by the Inventor in July, 2006 in Higashiomi, Shiga, Japan, of a proprietary selection of *Phlox drummondii* identified as code number 6Ph-16a, not patented, as the female, or seed, parent with a proprietary selection of *Phlox drummondii* identified as code number 0Ph-32a, not patented, as the male, or pollen, parent. The new *Phlox* plant was discovered and selected by the Inventor as a single flowering plant within the progeny of the stated cross-pollination in a controlled greenhouse environment in Higashiomi, Shiga, Japan in May, 2007.

Asexual reproduction of the new *Phlox* plant by cuttings in a controlled greenhouse environment in Higashiomi, Shiga, Japan since June, 2007 has shown that the unique features of this new *Phlox* plant are stable and reproduced true to type in successive generations.

SUMMARY OF THE INVENTION

Plants of the new *Phlox* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunphlosiro'. These characteristics in combination distinguish 'Sunphlosiro' as a new and distinct *Phlox* plant:

1. Compact and mounding plant habit.
2. Vigorous growth habit.
3. Freely branching and flowering habit.
4. Long flowering period.
5. White-colored flowers.
6. Good garden performance.

Plants of the new *Phlox* differ from plants of the female parent selection primarily in plant habit plants of the female parent selection are more compact than plants of the new *Phlox*. In addition, plants of the new *Phlox* are more heat tolerant than plants of the female parent selection.

Plants of the new *Phlox* differ from plants of the male parent selection primarily in flower size as plants of the male parent selection have smaller flowers. In addition, plants of the new *Phlox* are smaller than plants of the male parent selection.

Plants of the new *Phlox* can be compared to plants of *Phlox drummondii* 'Sunphloho', disclosed in U.S. Plant Pat. No. 16,724. In side-by-side comparisons conducted in Higashiomi, Shiga, Japan, plants of the new *Phlox* and 'Sunphloho' differed in the following characteristics:

1. Plants of the new *Phlox* were smaller and had shorter internodes than plants of 'Sunphloho'.
2. Plants of the new *Phlox* were not as upright as plants of 'Sunphloho'.

Plants of the new *Phlox* can be compared to plants of *Phlox drummondii* 'Sunphloconsa', disclosed in U.S. Plant Pat. No. 20,897. In side-by-side comparisons conducted in Higashiomi, Shiga, Japan, plants of the new *Phlox* and 'Sunphloconsa' differed in the following characteristics:

1. Plants of the new *Phlox* were shorter than plants of 'Sunphloconsa'.
2. Plants of the new *Phlox* were more freely flowering than plants of 'Sunphloconsa'.
3. Plants of the new *Phlox* and 'Sunphloconsa' differed in flower color.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph at the top of the sheet comprises a side perspective view of a typical flowering plant of 'Sunphlosiro' grown in a container.

The photograph at the bottom of the sheet is a close-up view of a typical flowering plant of 'Sunphlosiro'.

DETAILED BOTANICAL DESCRIPTION

The aforementioned photographs and following observations, measurements and values describe plants grown during the late spring in 15-cm containers in an outdoor nursery in Higashiomi, Shiga, Japan and under commercial cultural practices. During the production of the plants, day temperatures averaged 25° C. and night temperatures averaged 15° C. Plants were seven months old when the description and photographs were taken. In the following description, color references are made to The Royal Horticultural Society Colour Chart, 2001 Edition, except where general terms of ordinary dictionary significance are used.

Botanical classification: *Phlox drummondii* 'Sunphlosiro'.

Parentage:

*Female, or seed, parent*.—Proprietary selection of *Phlox drummondii* identified as code number 6Ph-16a, not patented.

*Male, or pollen, parent*.—Proprietary selection of *Phlox drummondii* identified as code number 0Ph-32a, not patented.

Propagation:

*Type*.—By cuttings.

*Time to initiate roots*.—About two to three weeks at 20° C. to 25° C.

*Time to produce a rooted young plant*.—About one to two months at 20° C. to 25° C.

*Root description*.—Fibrous; white in color.

*Rooting habit*.—Freely branching; medium density.

Plant description:

*Plant and growth habit*.—Compact and mounding plant habit; vigorous growth habit; freely branching habit with lateral branches potentially developing at every node; pinching enhances lateral branch development.

*Plant height*.—About 13.4 cm.

*Plant width (spread)*.—About 30.4 cm.

*Lateral branches*.—Length: About 15 cm. Diameter: About 2 mm. Internode length: About 1.2 cm. Strength: Strong. Texture: Pubescent. Color: Close to 145A.

Foliage description:

*Arrangement*.—Alternate, simple; sessile.

*Length*.—About 4.6 cm.

*Width*.—About 1.3 cm.

*Shape*.—Narrowly elliptic.

*Apex*.—Acute.

*Base*.—Obtuse.

*Margin*.—Entire.

*Texture, upper and lower surfaces*.—Pubescent.

*Venation pattern*.—Pinnate, reticulate.

*Color*.—Developing and fully expanded leaves, upper surface: Close to 137B; venation, close to 145C. Developing and fully expanded leaves, lower surface: Close to 138B; venation, close to 145C.

Flower description:

*Flower arrangement and habit*.—Single rotate flowers arranged in terminal and axillary cymes; flowers face mostly upright; cymes roughly hemispherical in shape; freely flowering habit with about 89 flowers per plant.

*Fragrance*.—Present, pleasant.

*Natural flowering season*.—Plants begin flowering about one month after planting; plants flower continuously from spring to autumn in Japan.

*Postproduction longevity*.—Flowers last about five days on the plant; flowers not persistent.

*Flower buds*.—Height: About 1.9 cm. Diameter: About 3.4 mm. Shape: Clavate. Color: Close to 150D.

*Inflorescence height*.—About 2.7 cm.

*Inflorescence diameter*.—About 5.3 cm.

*Flower diameter*.—About 2.7 cm.

*Flower depth*.—About 1.7 cm.

*Tube length*.—About 1.4 cm.

*Tube diameter, base*.—About 1.8 mm.

*Petals*.—Quantity per flower: Typically five in a single whorl; petals fused at the base into a narrow tube. Length: About 1.3 cm. Lobe width: About 1.4 cm. Shape: Broadly ovate. Apex: Broadly acute. Margin: Entire. Texture, upper and lower surfaces and throat: Smooth, glabrous. Texture, tube: Pubescent. Color: Developing and fully expanded petals, upper surface: Close to N155A. Developing and fully expanded petals, lower surface: Close to N155A. Throat: Close to 150D. Tube: Close to 150D.

*Sepals*.—Quantity per flower: Typically five in a single whorl, fused towards the base; calyx star-shaped. Length: About 7.8 mm. Width: About 1.8 mm. Shape: Lanceolate. Apex: Acute. Margin: Entire. Texture, upper and lower surfaces: Smooth, glabrous. Color, developing and fully expanded sepals, upper surface: Close to 137B. Color, developing and fully expanded sepals, lower surface: Close to 137C.

*Peduncles*.—Length: About 9 mm. Diameter: About 1 mm. Strength: Strong. Texture: Pubescent. Color: Close to 145A.

*Pedicels*.—Length: About 6 mm. Diameter: About 0.8 mm. Strength: Strong. Texture: Pubescent. Color: Close to 145B.

*Reproductive organs*.—Stamens: Quantity per flower: Typically five. Stamen length: About 7 mm. Anther shape: Lanceolate. Anther size: About 2.5 mm by 0.8 mm. Anther color: Close to 3A. Pollen amount: Moderate. Pollen color: Close to 6A. Pistils: Quantity per flower: One. Pistil length: About 3.5 mm. Stigma shape: Three-parted. Stigma color: Close to 145C. Style color: Close to 145C. Ovary color: Close to 143C.

*Seeds and fruits*.—Seed and fruit development have not been observed on plants of the new *Phlox*.

Disease & pest resistance: Plants of the *Phlox* have not been observed to be resistant to pathogens and pests common to *Phlox*.

Garden performance: Plants of the new *Phlox* have been observed to have good garden performance and to tolerate rain, wind and temperatures ranging from about 0° C. to about 35° C.

It is claimed:

1. A new and distinct *Phlox* plant named 'Sunphlosiro' as illustrated and described.

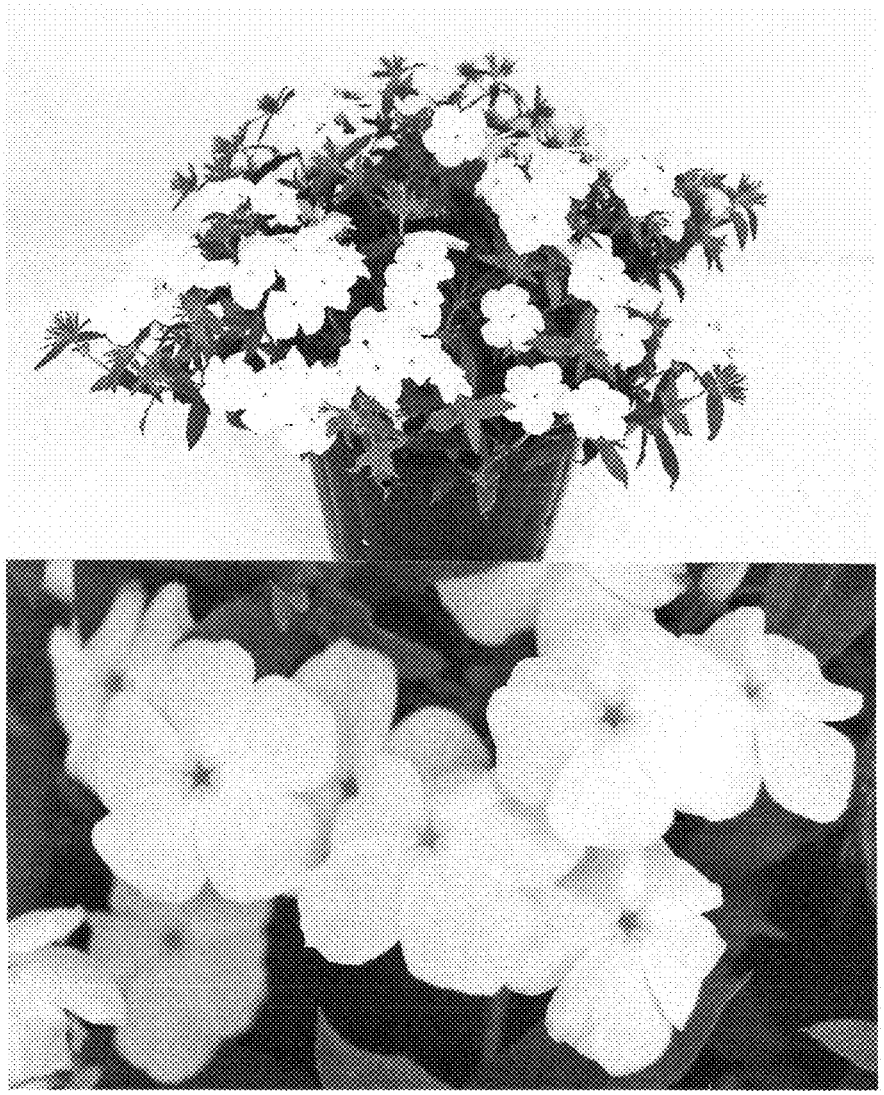

* * * * *